(12) United States Patent
Litsch

(10) Patent No.: US 12,412,303 B2
(45) Date of Patent: Sep. 9, 2025

(54) METHOD FOR OPERATING A SURGICAL MICROSCOPE, AND SURGICAL MICROSCOPE

(71) Applicant: Carl Zeiss Meditec AG, Jena (DE)

(72) Inventor: Dominik Litsch, Schorndorf (DE)

(73) Assignee: CARL ZEISS MEDITEC AG, Jena (DE)

( * ) Notice: Subject to any disclaimer, the term of this patent is extended or adjusted under 35 U.S.C. 154(b) by 466 days.

(21) Appl. No.: 17/715,938

(22) Filed: Apr. 7, 2022

(65) Prior Publication Data
US 2022/0343539 A1    Oct. 27, 2022

(30) Foreign Application Priority Data

Apr. 22, 2021 (DE) ...................... 10 2021 204 033.0

(51) Int. Cl.
*G06T 7/80* (2017.01)
*A61B 90/20* (2016.01)
*G02B 21/36* (2006.01)

(52) U.S. Cl.
CPC ................ *G06T 7/80* (2017.01); *A61B 90/20* (2016.02); *G02B 21/367* (2013.01); *G06T 2207/10056* (2013.01)

(58) Field of Classification Search
CPC .............................. G06V 10/16; G06V 10/245
USPC ........................................................ 359/383
See application file for complete search history.

(56) References Cited

U.S. PATENT DOCUMENTS

| 5,663,806 A * | 9/1997 | Grise ..................... H04N 1/128 358/406 |
| 6,978,052 B2 * | 12/2005 | Beged-Dov ........... G06T 3/4038 382/284 |
| 10,324,281 B2 | 6/2019 | Wilzbach et al. |
| 10,976,531 B2 * | 4/2021 | Lee ......................... A61B 90/25 |
| 2005/0163398 A1 * | 7/2005 | Ioka .......................... G06T 5/50 382/284 |
| 2017/0082847 A1 * | 3/2017 | Wilzbach ............... A61B 34/20 |
| 2018/0364469 A1 * | 12/2018 | Sakamoto ............ G02B 21/244 |
| 2019/0107700 A1 | 4/2019 | Lee et al. |

(Continued)

FOREIGN PATENT DOCUMENTS

| DE | 102011086666 A1 | 5/2013 |
| DE | 102014210053 A1 | 12/2015 |

(Continued)

*Primary Examiner* — Wyatt A Stoffa
*Assistant Examiner* — Seth D Moser
(74) *Attorney, Agent, or Firm* — NIXON PEABODY LLP; Jeffrey L. Costellia

(57) ABSTRACT

A method for operating a surgical microscope and microscope are disclosed, wherein at least one main image of a capture region, which is imaged through a beam path of an imaging optical unit of the surgical microscope, is captured by means of at least one main camera arranged in or at the beam path, wherein at least one additional image is captured by means of at least one additional camera arranged outside the beam path, wherein a capture region of the at least one additional camera at least partially overlaps with the imaged capture region of the at least one main camera, wherein the captured at least one main image and additional image are compared by an image processing device, and wherein, at least one correction parameter for the at least one main image is determined and provided.

6 Claims, 5 Drawing Sheets

(56) References Cited

U.S. PATENT DOCUMENTS

2021/0128266 A1* 5/2021 Wood .................. A61B 90/30
2021/0157112 A1 5/2021 Raab et al.

FOREIGN PATENT DOCUMENTS

| DE | 102016217628 A1 | 3/2018 |
| DE | 102019131646 A1 | 5/2021 |
| WO | WO-2007/100303 A1 | 9/2007 |
| WO | WO-2019/210322 A1 | 10/2019 |

* cited by examiner

METHOD FOR OPERATING A SURGICAL MICROSCOPE, AND SURGICAL MICROSCOPE

CROSS-REFERENCE TO RELATED APPLICATIONS

The present application claims the benefit of and priority to German Patent Application No. 10 2021 204 033.0, filed Apr. 22, 2021, the contents of which are hereby incorporated by reference herein in their entirety.

The invention relates to a method for operating a surgical microscope and to a surgical microscope.

When using surgical microscopes in connection with a navigation system (for example by Optinav or Brainlab), it is possible to overlay preoperative image data with captured real-time images. This can take place both in the surgical microscope itself by means of one or more micro-displays and also on a display device independently of the surgical microscope.

In the case of such an overlay, ideally all image data must be aligned with one coordinate system. In surgical microscopes having an optical viewing system for a surgeon, this is typically realized in the form of crosshairs arranged inside a tube, which can also be referred to as zero tube. The following imaging systems, for example, must be adjusted or calibrated to such a zero tube (or another reference element): cameras at the beam paths (mono or stereo), data superposition (micro-displays mono or stereo) and/or tracking components of a navigation system, such as for example antennas or marks or additional vicinity cameras that capture the surgical microscope. In purely digital surgical microscopes without an optical viewing system, one of the two main cameras is generally the leading one, to which the imaging systems are calibrated or adjusted.

Any error in the adjustment or calibration results in an error in the overlay of the data of the navigation with the real-time image. Since antennas of the navigation systems can additionally not be calibrated or adjusted to a zero tube but only to the cameras of the beam paths, a tolerance chain becomes longer, which can result in even greater errors.

One main problem when adjusting and calibrating is in particular a continuous magnification (zoom) and a continuous focus of the beam paths or of an imaging optical unit of the surgical microscope. Typically, this focus does not extend along an ideal optical axis of the zero tube, but is displaced in all six degrees of freedom. Since such displacements are partially reproducible, they can be corrected by calibration in the digital image. However, a non-reproducible error is not able to be corrected by calibration and thus remains.

DE 10 2014 210 053 A1 discloses a surgical system, comprising a surgical microscope with an imaging optical unit and a control unit for setting imaging parameters of the surgical microscope, an image processing device for overlaying an overlay image stored in the image processing device with an image that is generated by the surgical microscope, and a data processing unit that is connected to the control unit of the surgical microscope and to the image processing device, wherein the control unit is designed to store, before at least one imaging parameter of the surgical microscope is changed from a first value to a second value, both the first and also the second value and to make them available to the data processing unit, and wherein the image processing device is designed such that it modifies the overlay image in accordance with the stored first and second values of the at least one imaging parameter.

The invention is based on the object of providing a method for operating a surgical microscope and a surgical microscope, with which in particular a displacement of an optical axis of an imaging optical unit of a surgical microscope occurring when a magnification and/or a focus is/are changed can be corrected in an improved manner.

According to the invention, the object is achieved by a method having the features of patent claim 1 and a surgical microscope having the features of patent claim 5. Advantageous configurations of the invention emerge from the dependent claims.

It is one of the basic ideas of the invention to use at least one additional camera that is arranged outside a beam path of the surgical microscope. The at least one additional camera has a capture region that at least partially overlaps with a capture region of one or more main cameras of the surgical microscope that are arranged in or at the beam path. In this way, an additional image, which is captured by the at least one additional camera, can be used as a reference in order to be able to assess one or more main images, which are captured by means of the at least one main camera, with respect to a position. It is possible hereby in particular to provide a reference for main images which are captured at different magnifications and/or at different foci. Proceeding from a comparison result of a comparison of a main image with an additional image, which is captured as a reference, at least one correction parameter is determined and provided for the main image. The captured main image can be corrected by means of said at least one correction parameter. A correction can here be made in particular with respect to locating the main image within a coordinate system, for example by changing, in particular correcting, position information of the main image proceeding from the at least one correction parameter.

In particular, a method for operating a surgical microscope is made available, wherein at least one main image of a capture region, which is imaged through a beam path of an imaging optical unit of the surgical microscope, is captured by means of at least one main camera arranged in or at the beam path, wherein at least one additional image is captured by means of at least one additional camera arranged outside the beam path, wherein a capture region of the at least one additional camera at least partially overlaps with the imaged capture region of the at least one main camera, wherein the captured at least one main image and the captured at least one additional image are compared with one another by means of an image processing device, and wherein, proceeding from a comparison result, at least one correction parameter for the at least one main image is determined, and wherein the determined at least one correction parameter is provided.

Furthermore, in particular a surgical microscope is created, comprising at least one main camera in or at a beam path of an imaging optical unit of the surgical microscope, configured for capturing at least one main image of a capture region imaged through the beam path, at least one additional camera configured for capturing at least one additional image, wherein the at least one additional camera is arranged outside the beam path such that a capture region of the at least one additional camera at least partially overlaps with the imaged capture region, and an image processing device, wherein the image processing device is configured to compare the captured at least one main image and the captured at least one additional image with one another and to determine and provide, proceeding from a comparison result, at least one correction parameter for the at least one main image.

The method and the surgical microscope have the advantage that even non-reproducible errors that occur when a magnification and/or a focus is/are changed in the at least one main camera due to a movement of the optical axis of the beam path of the surgical microscope can be determined and corrected or at least taken into account. In this way, working with data superposition (augmentation) and/or navigation systems can be improved because in particular locating the at least one main image in a common coordinate system can be improved.

The surgical microscope can be monoscopic or stereoscopic. In particular, the surgical microscope is a stereoscopic surgical microscope. The surgical microscope in this case has two main cameras, which each capture at least one main image. The beam path of the surgical microscope is correspondingly designed for stereoscopic capturing. Accordingly, in each case at least one correction parameter is determined and provided for the main images captured by means of the two main cameras.

The imaging optical unit of the beam path of the surgical microscope has in particular movable lens elements, by means of which a magnification and/or a focus can be changed, in particular continuously. The surgical microscope furthermore has one or more micro-displays, with which image data, for example preoperative image data, can be superposed into a beam path by means of splitter mirrors, with the result that a user can perceive both the imaged capture region and also image data that are overlaid thereon. Furthermore, the surgical microscope can have a tracking or navigation system or form a surgical system with one.

The at least one main camera and the at least one additional camera may be adjusted and/or calibrated with respect to one another. The determination of the at least one correction parameter can hereby be further improved. A calibration can be performed for example by means of a chessboard or ChArUco board. In principle, such an adjustment or calibration is not necessary, however.

The at least one correction parameter is in particular a parameter that defines and/or corrects a position within a coordinate system that is used as a common reference. The at least one correction parameter can comprise in particular a position difference and/or a position. For example, a position of the at least one main image can be defined and/or corrected in a common coordinate system by means of the at least one correction parameter. The common coordinate system here serves in particular as a common reference system for superposing image data by means of micro-displays and for the connection of a navigation system. In particular, the captured at least one additional image serves as a reference for the common coordinate system.

Parts of the image processing device can be embodied, either individually or together, as a combination of hardware and software, for example as program code that is executed on least one microcontroller or microprocessor. However, it may also be possible for parts to be designed as application-specific integrated circuits (ASICs) or field-programmable gate arrays (FPGAs), either on their own or in combination. In particular, the image processing device comprises at least one computing device, for example a microcontroller or microprocessor, and at least one memory. It may also be possible for the image processing device to be provided as part of a control device of the surgical microscope.

In one embodiment, the at least one additional camera has a fixed focus and a fixed magnification. In this way, an error caused by the at least one additional camera can be minimized. Alternatively, the additional camera can have a variable magnification and/or a variable focus, in which an error is less significant than in the imaging optical unit of the surgical microscope. For example, this can be implemented by way of discrete magnification steps, which are achieved by mechanically highly precise stops.

In one embodiment, at least one calibration parameter is produced and/or changed proceeding from the determined at least one correction parameter. In this way it is possible, proceeding from the at least one correction parameter, for a calibration to be directly adapted such that, after the adaptation, individual image sources can once again be placed on top of one another with a precise fit and positioning. For example, it is possible hereby to improve superposition of preoperatively captured image data in an optical viewing system of the surgical microscope by means of micro-displays. Due to the at least one correction parameter or the at least one calibration parameter, it is possible to place or represent the images on top of one another with a more accurate position, with the result that superposed image data and the imaged capture region can be perceived congruently by a surgeon or other observer. It is hereby possible to improve a workflow during surgery and/or assisting.

In one embodiment, a plurality of main images are captured at different foci and/or different magnifications, wherein the at least one correction parameter is determined by comparison on the basis of the plurality of captured main images and the at least one captured additional image. In this way, any deviations that occur when changing the magnification and/or the focus in the at least one main camera can be determined and taken into account. For example, it is possible to run through a magnification and/or a focus within a specified parameter range and in each case to capture one main image at specified intervals by means of the at least one main camera. By comparing the captured main images with at least one captured additional image, the at least one correction parameter for the at least one main image is subsequently determined and provided. The at least one correction parameter is determined and provided in particular in dependence on the respective magnification and/or the respective focus.

In a corresponding embodiment of the surgical microscope, the image processing device is configured to determine the at least one correction parameter by comparison on the basis of a plurality of captured main images, which were captured at different foci and/or different magnifications by means of the at least one main camera, and the at least one captured additional image.

In a developing embodiment, a displacement, which occurs when the focus and/or the magnification is changed, of at least one image element and/or image region and/or feature in the captured main images is determined in comparison with the captured at least one additional image, wherein the at least one correction parameter is determined taking into account the determined displacement. The displacement is in particular a displacement in the x- and y-directions with respect to the image elements of the images. In the simplest case, for example an image region at the center of the at least one main image can be considered and evaluated. Ideally, the optical axis does not change during the magnification, which means that the image region at the center, for example a center point, should not be displaced in comparison with the captured at least one additional image. In the case of the focus, by contrast, the image region at the center, for example the center point, should be displaced at least along a straight line (since the optical axes of the main camera and additional camera are arranged at a fixed angle with respect to one another, this straight line is known). If this is the case, the optical axis does not change when the focus is changed. However, if the region at the center, for example the center point, is displaced when the magnification is changed, said displacement can be determined and the at least one correction parameter can be determined from the determined displacement. In particular, it is possible to determine from the displacement a position difference as a correction parameter, which can be subsequently evaluated for correcting a position of image elements in relation to a coordinate system. In addition to the region at the center, other regions can also be evaluated. For example, a displacement of an image region during an increasing magnification can be determined and evaluated. In the case of a small magnification, image elements and/or features located around a region of the center can be viewed in the captured at least one main image, which elements and/or features should, when the magnification increases, ideally move along a straight line in the direction of the outer image elements, because the magnification increases and the captured detail of the previously captured capture region becomes successively smaller (this straight line is known and in the ideal case should always also intersect the image center). In the case of a deviation from a movement along a straight line, this deviation or displacement can be evaluated and be used to determine the at least one correction parameter.

In a corresponding embodiment of the surgical microscope, the image processing device is configured to determine a displacement, which occurs when the focus and/or the magnification is changed, of at least one image element and/or image region and/or feature in the captured main images in comparison with the captured at least one additional image and to determine the at least one correction parameter taking into account the determined displacement.

In one embodiment, at least one mark is projected at least into an overlap region of the capture regions by means of a projection device, wherein the at least one projected mark contained in the captured images is evaluated during the comparison. In this way, a reference element that is easy to capture and evaluate can be produced in the captured images. The projection device can, by way of example, be a laser. Furthermore, even a laser used in an autofocus of the at least one main camera can be used. The projection device can also operate in the infrared, with the result that a surgeon and/or an assistant cannot perceive the mark. A projected mark can here comprise for example a pattern, for example a cross and/or a grid etc.

In a corresponding embodiment of the surgical microscope, the surgical microscope comprises at least one projection device, wherein the at least one projection device is configured to project at least one mark at least into one overlap region of the capture region, wherein the image processing device is furthermore configured to evaluate the at least one projected mark contained in the captured images during the comparison.

In one embodiment, the comparison is performed by means of at least one of the following methods: correlation, dense/non-dense feature extraction, artificial intelligence, machine learning and/or image registration methods. In principle, it is possible to use methods of computer vision that are known per se during the evaluation by means of the image processing device.

When comparing by means of correlation, one of the captured images is kept fixed and the other image is slid, image element by image element, over the fixed image (in the x- and y-directions), wherein a correlation coefficient is determined for each position as a quality measure. The correlation coefficient is or becomes a maximum if the two images are correctly placed one on top of another. From a difference value by which the other image was moved with respect to the fixed image in order to reach the maximum correlation coefficient it is possible to determine a displacement between the two images. In this case, it is possible that the images that are to be compared to one another are preprocessed before the comparison, for example by previously filtering the images (e.g. edge extraction filter etc.).

In the case of the dense feature extraction, each image element is viewed in a captured image. In the case of the non-dense feature extraction, by contrast, only representative image elements are viewed in the captured image. Examples to be mentioned are the methods SIFT (scale-invariant feature transform), SURF (speeded-up robust features) and ORB (oriented FAST and rotated BRIEF). These methods are feature extractors and descriptors, which is to say they determine in a first step (key point extraction) characteristic image elements in the image (e.g. edges and corners over different scales). These key points are then described by descriptors (a vector with numbers) (for example in the form of an analysis of image elements in an area around the key point, for example as histograms, etc.). In order to determine a displacement between two images, that is to say between a captured main image and a captured additional image, for example key points and descriptors are determined in each case in both images. The result is a list of key points with a corresponding description for each image. As a next measure, corresponding key points between the images are identified. This is done by comparing the descriptors (e.g. in the form of a nearest neighbor search). The list of the corresponding key points can be used to estimate a transformation (here in particular rigid transformation) between the images. Since there are generally significantly more key point pairs than parameters of the transformation, the problem is over determined. For this reason, for example the RANSAC (random sample consensus) method can be applied to make the determination of the transformation more robust. The determined transformation then provides in particular the at least one correction parameter, in particular in the form of a position difference between the images. In principle, it is also possible to additionally or alternatively use other methods of computer vision.

By means of artificial intelligence and/or machine learning, it is possible in particular to train features and their descriptions. Subsequently, for example the previously described methods can be used to determine the at least one correction parameter. Furthermore, it is also possible to estimate the at least one correction parameter by means of artificial intelligence and/or machine learning. In this case, for example a method of machine learning, in particular an artificial neural network, is trained by means of pairs of images, that is to say in each case of one main image and one additional image, whose relative displacement is known as an annotation or ground truth. In particular, a convolutional neural network (CNN) is used here, which learns the feature description in a first part. In a second part, it is learned how the displacement is determined or estimated from the feature description. Subsequently, the trained machine learning method, in particular the trained artificial neural network, can be applied, during an application or inference phase, to pairs of in each case one main image and one additional image and estimate a displacement for them (in particular a displacement in the x- and y-directions with respect to the image elements, that is to say in particular a position difference).

By means of methods of image registration that are known per se, different images comprising the same scene, in the present case the same capture region, can be made to correspond. From a transformation taking place as part of the image registration, the parameters used herein can be evaluated to determine a displacement between the images, that is to say between the main image and the additional image, and furthermore determine herefrom the at least one correction parameter.

The invention is explained in greater detail below on the basis of preferred exemplary embodiments with reference to the figures. In the figures:

FIG. 1 shows a schematic illustration of one embodiment of the surgical microscope 1. The method described in this disclosure will be explained in more detail with reference to the surgical microscope 1.

Figure 1:
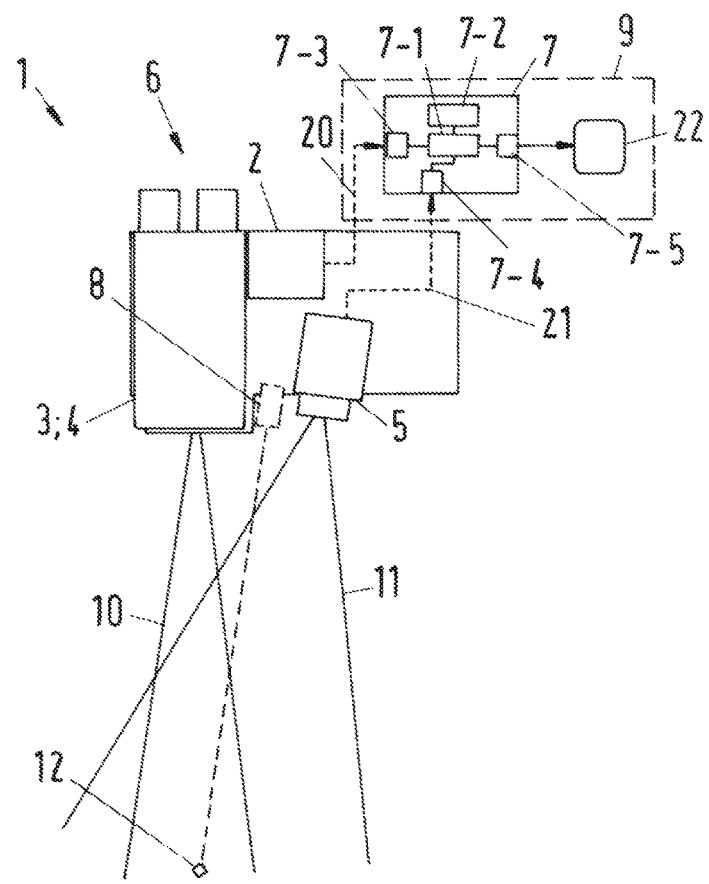
FIG. 1 shows a schematic illustration of one embodiment of the surgical microscope.

The surgical microscope 1 comprises a main camera 2, which is arranged at a beam path 3 of an imaging optical unit 4. The beam path 3 and the imaging optical unit 4 are illustrated in a simplified and schematic manner. The imaging optical unit 4 comprises in particular movable lens elements (not shown), with which a magnification and/or a focus can be continuously set. The surgical microscope 1 furthermore comprises an additional camera 5, which is arranged outside the beam path 3 of the surgical microscope 1, and an image processing device 7. The image processing device 7 can be designed to be part of a control device 9 of the surgical microscope.

If the surgical microscope 1 is a stereoscopic surgical microscope 1, the surgical microscope 1 comprises two main cameras 2, or the main camera 2 is a stereoscopic camera. No reference will be separately made below to the stereoscopic capturing; in principle, the method in a stereoscopic surgical microscope 1 is designed analogously for both main cameras 2.

The additional camera 5 may have a fixed focus and a fixed magnification.

The capture region 10 of the main camera 2 is congruent with an image that is imaged by the imaging optical unit 4 through the eyepieces of an optical viewing system 6 of the surgical microscope 1. A capture region 11 of the additional camera 5 at least partially overlaps with the capture region 10 of the main camera 2. In particular, the capture region 11 of the additional camera 5 completely comprises the capture region 10 of the main camera 2 in all stages of the magnification and/or of the focus.

In the embodiment shown, the additional camera 5 is arranged for this purpose on a side next to the beam path 3 or a tube of the surgical microscope 1. The additional camera 5 is arranged and aligned such that the capture region 11 comprises the capture region 10 of the main camera 2.

At least one main image 20 is captured by means of the main camera 2 and supplied to the image processing device 7 via an interface 7-3 that is configured for this purpose. The at least one main image 20 comprises in particular the capture region 10 of the main camera 2 or images it. At least one additional image 21 is captured by means of the additional camera 5 and supplied to the image processing device 7 via an interface 7-4 that is configured for this purpose. The at least one additional image 21 comprises in particular the capture region 11 of the additional camera 5 or images it.

The image processing device 7 comprises in particular a computing device 7-1 and a memory 7-2. The image processing device 7 is configured to compare the captured at least one main image 20 and the captured at least one additional image 21 with one another and to determine and provide, proceeding from a comparison result, at least one correction parameter 22 for the at least one main image 20. The at least one correction parameter 22 is provided for example as an analog or digital signal, for example as a data packet. In particular, the at least one correction parameter is output at an interface 7-5 that is configured for this purpose. For comparing the images 20, 21 and for determining the at least one correction parameter 22, the computing device 7-1 executes for example corresponding program code.

The at least one correction parameter 22 comprises in particular a position difference between the main image 20 and the at least one additional image 21, which is considered the reference. In particular, the at least one correction parameter 22 comprises a position difference with respect to a reference coordinate system, to which all image sources, i.e. in particular the main camera 2 and the additional camera 5, are adjusted and calibrated. Under the assumption that an additional image 21 captured by means of the additional camera 5 with respect to this reference coordinate system has a smaller error than the captured at least one main image 20, the additional image 21 can be considered the reference and an error of the position of the at least one main image 20 relative thereto can be determined.

Figure 2:
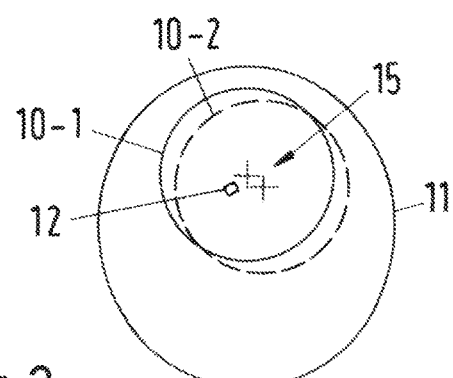
FIG. 2 shows a schematic illustration of a capture region of the main camera and of a capture region of the additional camera.

This is illustrated schematically in FIG. 2, which shows capture regions 10-x of the main camera 2 and the capture region 11 of the additional camera 5 in a top view, that is to say from the perspective of the cameras 2, 5. During the change of a magnification and/or a focus of the main camera 2, in which lens elements of the imaging optical unit 4 (FIG. 1) are moved, the capture region 10-x of the main camera 2 may become displaced, which is illustrated by way of example by the two illustrated capture regions 10-1, 10-2. In comparison with this, the capture region 11 of the additional camera 5 remains the same. The capture region 11 which remains constant is used according to the method as a reference in order to determine a displacement of the capture region 10-x of the main camera 2.

It is possible that a plurality of main images 20 are captured at different foci and/or different magnifications, wherein the at least one correction parameter 22 is determined by comparison on the basis of the plurality of captured main images 20 and the at least one captured additional image 21.

According to a development, a displacement, which occurs when the focus and/or the magnification is changed, of at least one image element and/or image region and/or feature in the captured main images 20 can be determined in comparison with the captured at least one additional image 21, wherein the at least one correction parameter 22 is determined taking into account the determined displacement.

The surgical microscope 1 (FIG. 1) may have a projection device 8, wherein the projection device 8 is configured to project a mark 12 at least into an overlap region of the capture regions 10, 11, wherein the image processing device 7 is furthermore configured to evaluate the projected mark 12 contained in the captured images 20, 21 during the comparison. Since the projected mark 12 remains spatially fixed in the additional image 21 and has known properties in terms of shape, a displacement of the capture regions 10-1, 10-2 of the main camera can be determined and evaluated in a particularly simple and efficient manner. The projection device 8 can be a laser that emits for example in the visible or infrared wavelength range and projects the mark 12, for example a cross, a pattern, or a reference point, into the overlap region of the capture regions 10, 11.

In particular, the comparison is performed by means of at least one of the following methods: correlation, dense/non-dense feature extraction, artificial intelligence, machine learning and/or image registration methods.

Figure 3A:
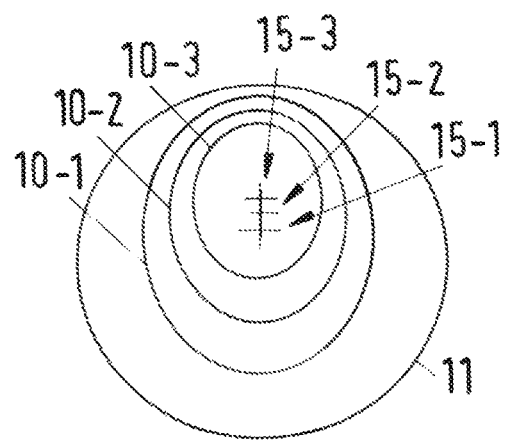
FIG. 3a shows a schematic illustration of a behavior of the capture regions with respect to one another when the focus is changed without errors.
Figure 3B:
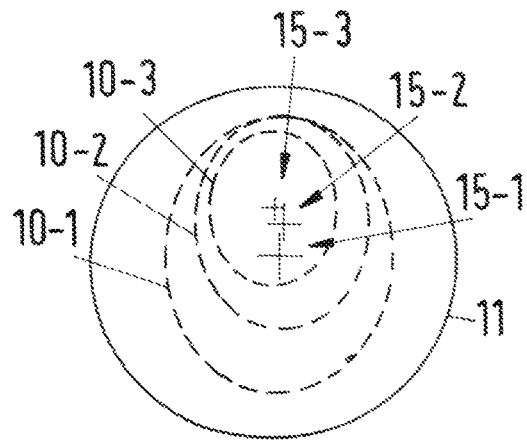
FIG. 3b shows a schematic illustration of a behavior of the capture regions with respect to one another when the focus is changed with errors.

FIGS. 3a and 3b show schematic illustrations of the capture regions 10-x, 11 of the main camera and of the additional camera to elucidate the method. FIG. 3a shows a change in the capture region 10-x of the main camera when the focus is changed in different focal planes, when focusing takes place without errors, that is to say when an optical axis of the beam path of an imaging optical unit of the surgical microscope is not displaced during focusing. It shows that a center point 15-x of the respective capture regions 10-x lies along a straight line. FIG. 3b illustrates the capture regions 10-x in the same focal planes when focusing does not take place without errors, that is to say when an optical axis of the beam path of the imaging optical unit of the surgical microscope is displaced during focusing. It shows that the center points 15-x of the respective capture regions 10-x do not lie along a straight line.

The behavior shown in each case in FIG. 3a and FIG. 3b can be used to determine a displacement of the capture regions 10-x, 11 with respect to one another and, based on this, to determine the displacement of captured main images with respect to a captured additional image, because the capture regions 10-x, 11 directly correspond to the captured main images or the captured additional image. The captured images are compared with one another by means of the image processing device and the displacement, for example of the center point 15-x, is determined. It is possible to determine herefrom the at least one correction parameter for the main images.

Figure 4A:
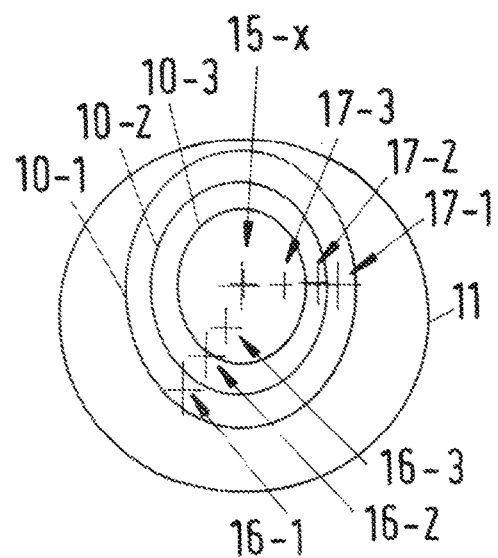
FIG. 4a shows a schematic illustration of a behavior of the capture regions with respect to one another when the magnification is changed without errors.
Figure 4B:
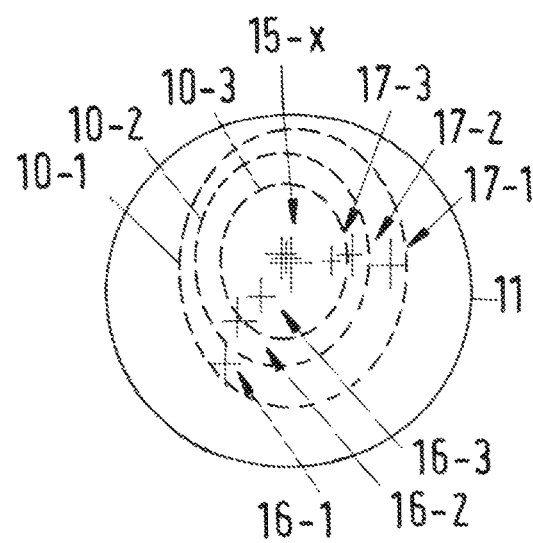
FIG. 4b shows a schematic illustration of a behavior of the capture regions with respect to one another when the magnification is changed with errors.

FIGS. 4a and 4b show a behavior when a magnification is changed. Here, FIG. 4a shows a behavior of the capture regions 10-x, 11 with respect to one another in the case of a magnification without errors, that is to say when the optical axis of the imaging optical unit of the surgical microscope is not displaced when the magnification is changed.

In the case of a magnification without errors, the center points 15-x remain spatially fixed (FIG. 4A), that is to say, the captured main images corresponding to the capture regions 10-x always show the same region in the center point 15-x that is also captured by the capture region 11 of the additional camera. In the case of a magnification without errors, regions 16-x, 17-x, which are located at the periphery of the capture regions 10-x, move in particular on a straight line toward the center point. In other words, in the case of a magnification without errors, an image element respectively corresponding to the capture region 10-x at the periphery of the associated captured main images moves along a straight line in the direction of the center point or images corresponding regions on this straight line.

FIG. 4b shows the behavior in the case of a magnification with errors, that is to say in the case of a magnification that is accompanied in particular by a displacement of the optical axis of the imaging optical unit of the surgical microscope. The center points 15-x of the capture regions 10-x of the main camera are displaced relative to the capture region 11 of the additional camera. Accordingly, the regions 16-x, 17-x, which are located at the periphery of the capture regions 10-x, or image elements corresponding thereto, are also displaced during the magnification not along a straight line extending in the direction of the center points 15-x but along a different path.

Figure 5:
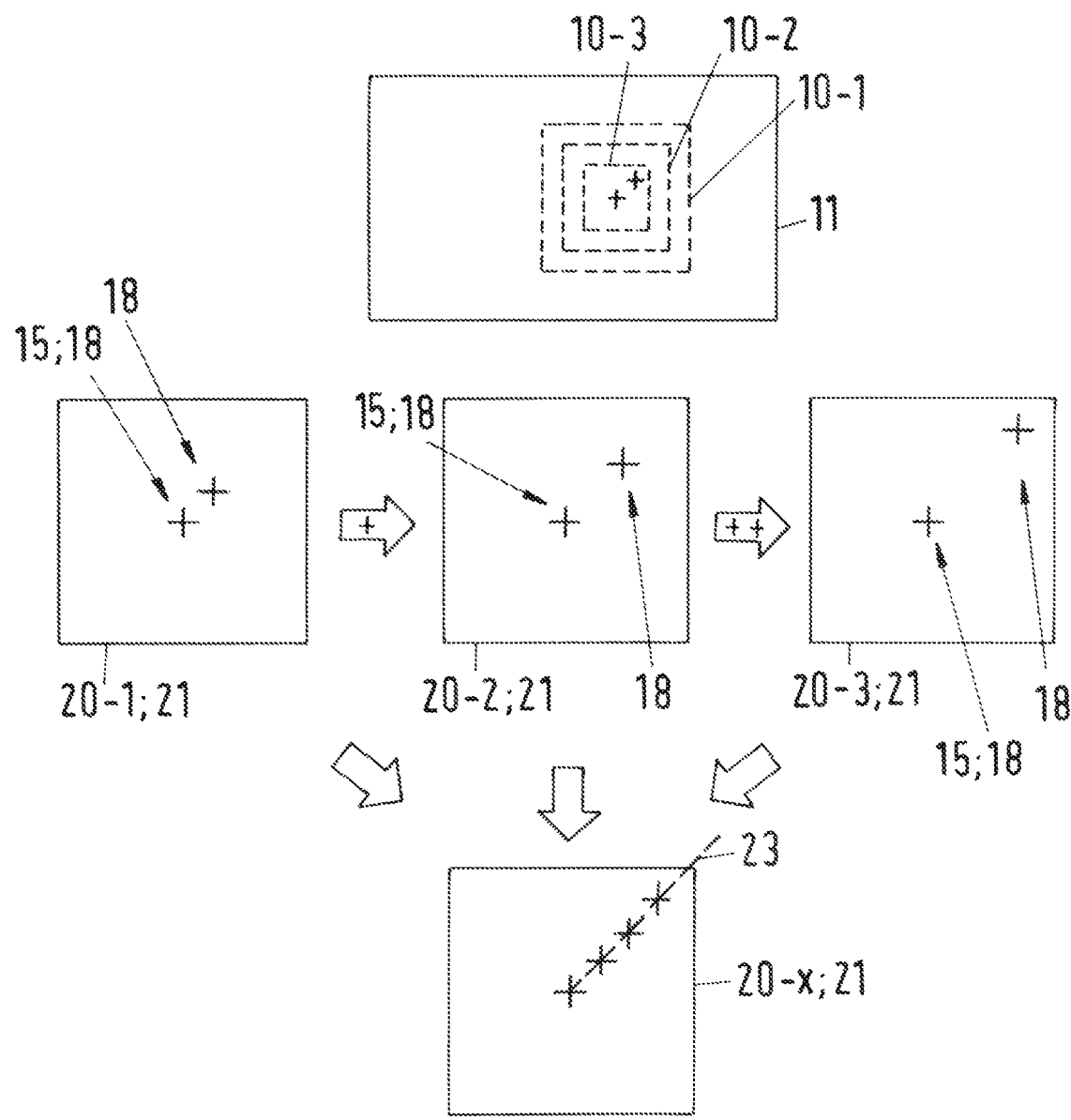
FIG. 5 shows a schematic illustration to elucidate a comparison of captured main images with a captured additional image when the magnification is changed without errors.

FIG. 5 shows a schematic illustration for elucidating a comparison of main images 20-x, captured at different magnifications and capture regions 10-x of the main camera, with an additional image 21, which is captured with a fixed capture region 11, when the magnification is changed without errors. For the capture region 11 of the additional camera, in each case only one detail of the additional image 21 that corresponds to the respective capture region 10-x of the main camera is shown in the middle row.

Since the optical axis of the imaging optical unit of the surgical microscope does not change when the magnification is changed, features 18 which are shown by way of example lie one above the other with a precise fit. In the various magnifications, the center point 15 remains in the same position, and the outer feature 18 moves along a straight line 23 extending in the direction of the center point 15 (FIG. 5, bottom). If a feature 18 lies at a known center point 15, for example at the x-y-image element coordinate 10/10, the feature 18 is displaced during the magnification in the ideal case illustrated here in particular toward the coordinates 11/11, 12/12 and 13/13 etc. A captured main image 20-x and a captured additional image 21 are compared with one another for example by means of a method explained in this disclosure, and the at least one correction parameter is determined on the basis of a comparison result. Since in the case of a magnification without errors the features 18 lie on top of one another with a perfect fit, the comparison does not result in a position difference between the main images 20-x and the additional image 21. Accordingly, the at least one correction parameter also includes no position difference.

Figure 6:
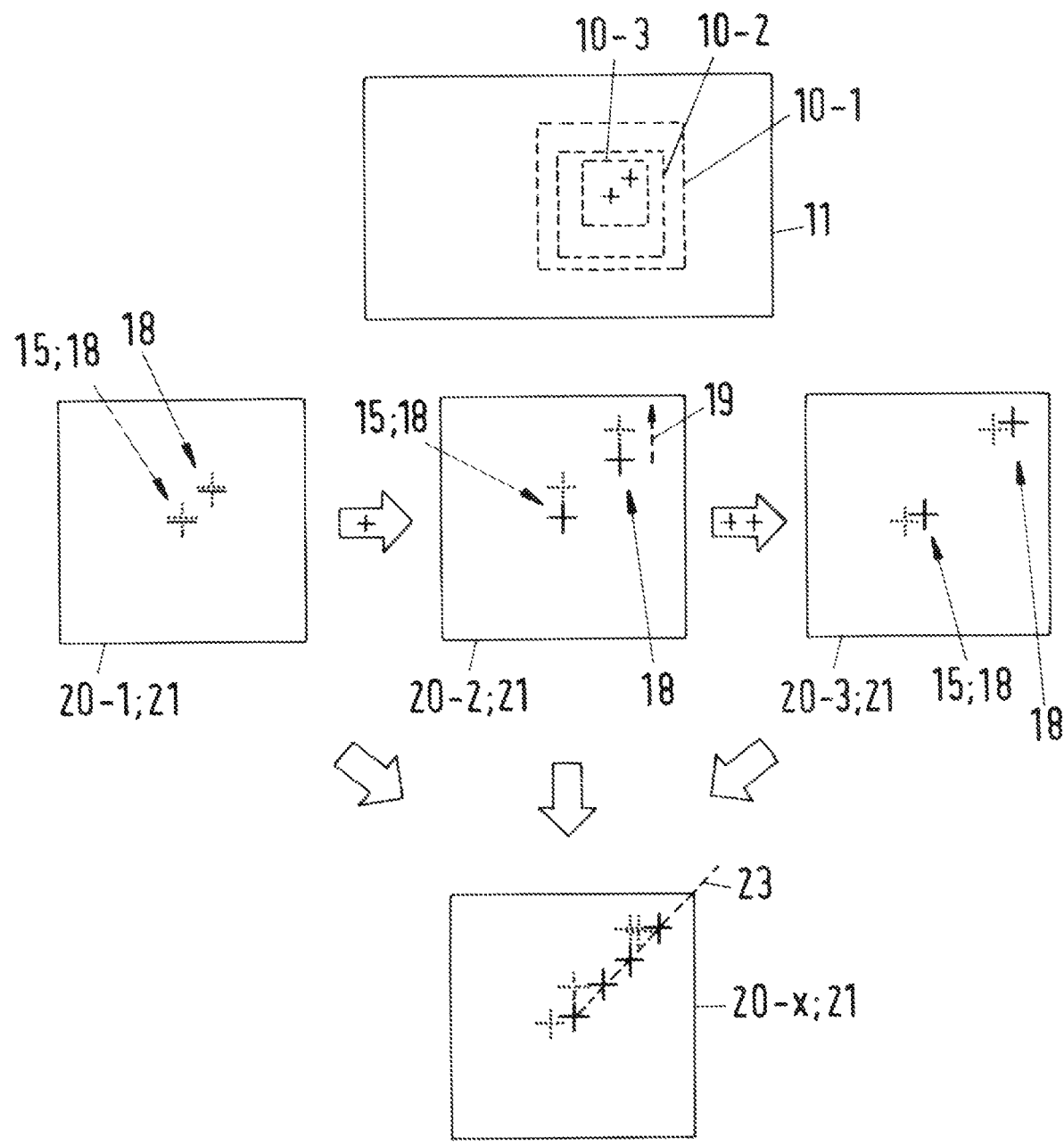
FIG. 6 shows a schematic illustration to elucidate a comparison of captured main images with a captured additional image when the magnification is changed with errors.

FIG. 6 shows a schematic illustration for elucidating a comparison of main images 20-x, captured at different magnifications and capture regions 10-x of the main camera, with an additional image 21, which is captured with a fixed capture region 11, when the magnification is changed with errors. For the capture region 11 of the additional camera, in each case only one detail of the additional image 21 that corresponds to the respective capture region 10-x of the main camera is shown here, too, in the middle row.

Since the optical axis of the imaging optical unit of the surgical microscope changes when the magnification is changed, features 18, which are shown by way of example, at different magnifications in images 20-x, 21 no longer lie one above the other with a precise fit. In the various magnifications, the center point 15 moves, and the outer feature 18 no longer moves along a straight line 23 extending in the direction of the center point 15 (FIG. 6, bottom). A captured main image 20-*x* and a captured additional image 21 are compared with one another for example by means of a method explained in this disclosure, and the at least one correction parameter is determined from a comparison result. Since in the case of a magnification with errors the features 18 no longer lie one above the other with a precise fit, the comparison results in a displacement 19 (for the sake of clarity shown only schematically at a feature 18) or a position difference between the main images 20-*x* and the additional image 21. Accordingly, the at least one correction parameter includes a position difference for at least the main images 20-2, 20-3. The position difference can be used to adjust or calibrate the respective main images 20-2, 20-3 again to the common coordinate system or the additional image 21 as a reference.

Figure 7:
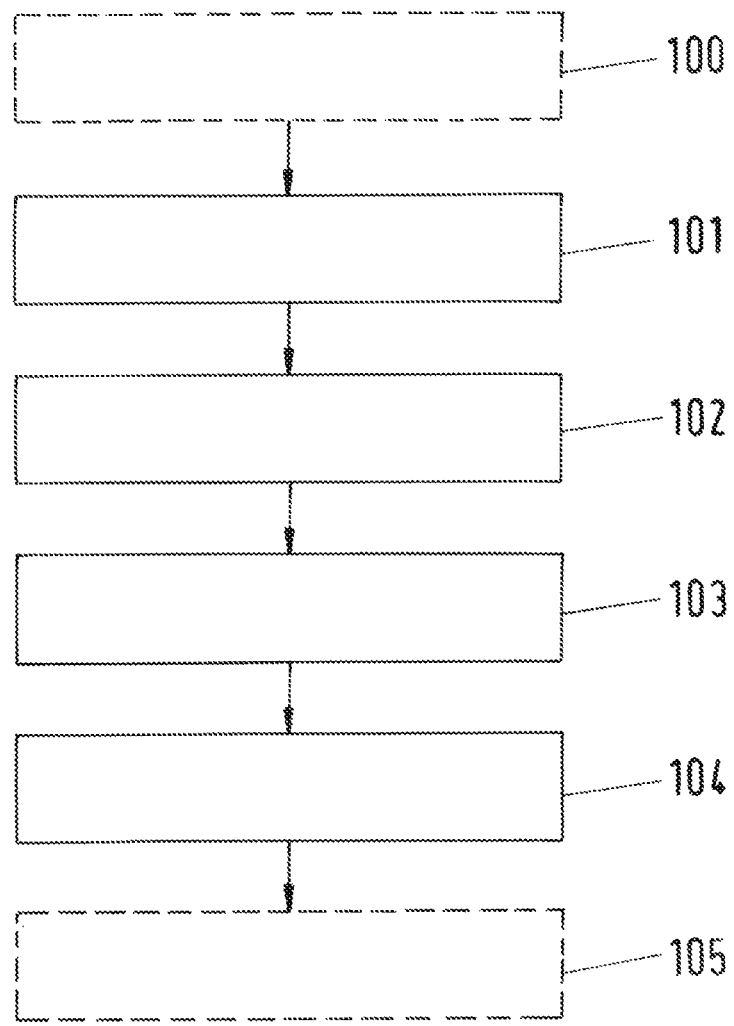
FIG. 7 shows a schematic flowchart of an embodiment of the method for operating a surgical microscope.

FIG. 7 shows a schematic flowchart of an embodiment of the method for operating a surgical microscope.

In a measure 101, at least one main image of a capture region imaged through a beam path of an imaging optical unit of the surgical microscope is captured by means of at least one main camera arranged in or at the beam path.

In a measure 102, at least one additional image is captured by means of at least one additional camera arranged outside the beam path, wherein a capture region of the at least one additional camera at least partially overlaps with the imaged capture region of the at least one main camera.

In a measure 103, the captured at least one main image and the captured at least one additional image are compared with one another by means of an image processing device. Proceeding from a comparison result, at least one correction parameter for the at least one main image is determined.

In measure 102, a displacement, which occurs when the focus and/or the magnification is changed, of at least one image element and/or image region and/or feature in the captured main images may be determined in comparison with the captured at least one additional image, wherein the at least one correction parameter is determined taking into account the determined displacement.

In particular, the comparison of the images in measure 103 is performed by means of at least one of the following methods: correlation, dense/non-dense feature extraction, artificial intelligence, machine learning and/or image registration methods.

In a measure 104, the determined at least one correction parameter is provided. The at least one correction parameter is provided for example as an analog or digital signal, for example as a data packet.

In a measure 105, at least one calibration parameter may be produced and/or changed proceeding from the determined at least one correction parameter. The at least one main camera can be calibrated with respect to the at least one additional camera or with respect to the capture region thereof by means of the at least one calibration parameter.

In measure 103, a plurality of main images may be captured at different foci and/or different magnifications, wherein the at least one correction parameter is determined by comparison on the basis of the plurality of captured main images and the at least one captured additional image.

Furthermore, in a measure 100, at least one mark may be projected into an overlap region of the capture regions by means of a projection device, wherein the at least one projected mark contained in the captured images is evaluated during the comparison in measure 103.

LIST OF REFERENCE SIGNS

1 Surgical microscope
2 Main camera
3 Beam path
4 Imaging optical unit
5 Additional camera
6 Optical viewing system
7 Image processing device
7-1 Computing device
7-2 Memory
7-3 Interface
7-4 Interface
7-5 Interface
8 Projection device
9 Control device
10 Capture region (main camera)
10-*x* Capture region (main camera)
11 Capture region (additional camera)
12 Mark
15-*x* Center point
16-*x* Region (at the periphery)
17-*x* Region (at the periphery)
18 Feature
19 Displacement
20 Main image
20-*x* Main image
21 Additional image
22 Correction parameter
23 Straight line
100-105 Measures of the method

The invention claimed is:

1. A method for operating a surgical microscope, the method comprising:
   capturing a plurality of main images of a main capture region at different foci and/or different magnifications, which is imaged through a beam path of an imaging optical unit of the surgical microscope, by at least one main camera arranged in or at the beam path,
   capturing at least one additional image by at least one additional camera arranged outside the beam path, wherein an additional capture region of the at least one additional camera at least partially overlaps with the main capture region of the at least one main camera,
   comparing the plurality of main images and the at least one additional image with one another by an image processing device to determine at least one correction parameter for at least one main image of the plurality of main images by comparison on a basis of the plurality of main images and the at least one additional image, and
   determining a displacement, which occurs when the focus and/or the magnification is changed, of at least one image element and/or image region and/or feature in the plurality of main images in comparison with the at least one additional image, wherein the at least one correction parameter is determined taking into account the determined displacement.

2. The method as claimed in claim 1, wherein at least one calibration parameter is produced and/or changed proceeding from the determined at least one correction parameter.

3. The method as claimed in claim 1, wherein at least one mark is projected at least into an overlap region of the main capture regions and the additional capture region by a laser, wherein the at least one projected mark contained in the plurality of main images and the at least one additional image is evaluated during the comparison.

4. The method as claimed in claim 1, wherein the comparison is carried out by at least one of the following methods: correlation, dense/non-dense feature extraction, artificial intelligence, machine learning and/or image registration methods.

5. A surgical microscope comprising:
at least one main camera in or at a beam path of an imaging optical unit of the surgical microscope, the at least one main camera configured for capturing a plurality of main images of a main capture region imaged through the beam path at different foci and/or different magnifications,
at least one additional camera configured for capturing at least one additional image, wherein the at least one additional camera is arranged outside the beam path such that an additional capture region of the at least one additional camera at least partially overlaps with the main capture region, and
an image processing device, wherein the image processing device is configured to compare the plurality of main images and the at least one additional image with one another and to determine, proceeding from a comparison result, at least one correction parameter for at least one main image of the plurality of main images by comparison on a basis of the plurality of main images and the at least one additional image,
wherein the image processing device is configured to determine a displacement, which occurs when the focus and/or the magnification is changed, of at least one image element and/or image region and/or feature in the plurality of main images in comparison with the at least one additional image and to determine the at least one correction parameter taking into account the determined displacement.

6. The surgical microscope as claimed in claim 5, wherein the at least one additional camera has a fixed focus and a fixed magnification.

* * * * *

UNITED STATES PATENT AND TRADEMARK OFFICE
CERTIFICATE OF CORRECTION

PATENT NO. : 12,412,303 B2  
APPLICATION NO. : 17/715938  
DATED : September 9, 2025  
INVENTOR(S) : Dominik Litsch Page 1 of 1

It is certified that error appears in the above-identified patent and that said Letters Patent is hereby corrected as shown below:

In the Claims

Column 12, Claim 3, Lines 66-67, "overlap region of the main capture regions" should read --overlap region of the main capture region--

Signed and Sealed this  
Thirtieth Day of December, 2025

John A. Squires  
*Director of the United States Patent and Trademark Office*